United States Patent [19]

Brunelle et al.

[11] Patent Number: 4,973,729
[45] Date of Patent: Nov. 27, 1990

[54] METHOD FOR PREPARING HYDROQUINONE AND HYDROQUINONE-BISPHENOL A BISCHLOROFORMATES

[75] Inventors: Daniel J. Brunelle, Scotia; David K. Bonauto, Schenectady, both of N.Y.

[73] Assignee: General Electric Company, Schenectady, N.Y.

[21] Appl. No.: 299,572

[22] Filed: Jan. 19, 1989

[51] Int. Cl.$^5$ .................. C07C 68/02; C07C 69/96
[52] U.S. Cl. .................. 558/281; 528/370; 528/372; 558/268
[58] Field of Search .................. 558/281

[56] References Cited

U.S. PATENT DOCUMENTS 4,638,077  1/1987  Brunelle et al. .................. 558/281

*Primary Examiner*—Vivian Garner
*Attorney, Agent, or Firm*—William H. Pittman; James C. Davis, Jr.

[57] ABSTRACT

Bischloroformates of bisphenol compositions comprising hydroquinone or a hydroquinone-bisphenol A mixture are prepared by passing phosgene into a vigorously agitated mixture of water, an alkaline earth metal hydroxide, the bisphenols and a substantially inert, water-immiscible organic liquid such as methylene chloride. The molar ratio of water to alkaline earth metal hydroxide is in the range of about 3–8:1. The bisphenols and at least a portion of the organic liquid are preferably initially present in the reaction mixture, and the alkaline earth metal hydroxide is preferably added during phosgenation.

17 Claims, No Drawings

METHOD FOR PREPARING HYDROQUINONE AND HYDROQUINONE-BISPHENOL A BISCHLOROFORMATES

This invention relates to the preparation of bischloroformates, and more particularly bischloroformates of hydroquinone and hydroquinone-containing mixtures.

The preparation of cyclic polycarbonate oligomers from bischloroformates is described, for example, in U.S. Pat. No. 4,644,053. Cyclic polycarbonate oligomer compositions are an extremely versatile class of intermediates for conversion to linear polycarbonates under a wide variety of reactive conditions.

An excellent method for preparing bischloroformates, disclosed in U.S. Pat. No. 4,638,077, involves the phosgenation of a bisphenol in a heterogeneous aqueous-organic mixture. The pH of the mixture, more particularly the aqueous phase thereof, is maintained in the range of about 0.5-8 by the addition of an aqueous alkali metal or alkaline earth metal base.

More recently, it has been discovered that cyclic polycarbonate oligomer compositions comprising bisphenol A units and hydroquinone units, the latter comprising at least 40% by number, may be converted into highly solvent-resistant polycarbonates. Certain of these polycarbonates, particularly those containing at least 60% hydroquinone units, are crystalline. Cyclic polycarbonate oligomer compositions of this type, and the method for their preparation, are disclosed and claimed in application Ser. No. 07/290,053. The solvent-resistant polycarbonates produced therefrom, and the method for their preparation, are similarly disclosed and claimed in Ser. No. 07/290,051. Both applications are copending and commonly owned herewith.

It has been found that the method described broadly in U.S. Pat. No. 4,638,077 is not satisfactory for the preparation of hydroquinone and mixed hydroquinone-bisphenol A bischloroformates. A primary factor appears to be the solubility of hydroquinone in water, which is much higher than that of bisphenol A. Thus, hydroquinone tends to dissolve in the aqueous phase, which minimizes contact with the phosgene which is in the organic phase. A related problem is the formation of large amounts of solids which accumulate between the aqueous and organic phases. These solids are believed to be hydroquinone carbonate bischloroformate oligomers, formed by reaction of the hydroquinone in the aqueous phase with any hydroquinone bischloroformate initially produced.

These problems are solved by the present invention which provides a method for the preparation of hydroquinone and hydroquinone-bisphenol A bischloroformates by phosgenation in a heterogeneous water-organic medium. Said method affords the desired bischloroformates in high yield and capable of easy isolation.

The invention is a method for preparing a bischloroformate composition which comprises passing phosgene into a vigorously agitated mixture of water; a substantially inert, water-immiscible organic liquid; an alkaline earth metal hydroxide; and a bisphenol composition comprising hydroquinone or a mixture of hydroquinone and bisphenol A containing at least 40 mole percent hydroquinone; the molar ratio of water to alkaline earth metal ion in said mixture being in the range of about 3-8:1.

The invention is applicable to the preparation of bischloroformates of bisphenol compositions comprising hydroquinone and mixtures of hydroquinone and bisphenol A, or 2,2-bis(4-hydroxyphenyl)propane. Such mixtures should contain at least 40 mole percent hydroquinone. The hydroquinone content is most often at least about 50 mole percent and preferably about 50-75 mole percent.

In addition to the bisphenol composition, the invention employs phosgene, a substantially inert, waterimmiscible organic liquid and an alkaline earth metal hydroxide. Illustrative hydroxides are magnesium hydroxide, calcium hydroxide and barium hydroxide; calcium hydroxide is often preferred because of its particular suitability, availability and low cost.

Suitable organic liquids are those which are inert and immiscible with water. They need not dissolve substantial amounts of bisphenol composition, but should be solvents for the bischloroformate product. Illustrative liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons are preferred, with methylene chloride being particularly preferred.

According to the invention, the bisphenol composition is combined with the organic liquid and phosgene is passed into the resulting heterogeneous mixture, generally at a temperature in the range of about 10°-40° C. The phosgene is ordinarily introduced in gaseous form, but its introduction as a liquid or as a solution in a suitable solvent is within the scope of the invention.

Also present in the reaction mixture are water and the alkaline earth metal hydroxide. The molar ratio of phosgene to bisphenol is most often the stoichiometric ratio for bischloroformate formation; i.e., about 2:1. However, an excess of phosgene, typically no greater than about 10%, may be employed.

Alkaline earth metal hydroxide may be employed in stoichiometric or greater than stoichiometric amounts. While no specific upper limit appears applicable, there is no particular benefit in employing an excessive amount; molar ratios of hydroxide to bisphenols in the bisphenol composition in the range of about 1-10:1 are generally suitable. It is sometimes found that in the phosgenation of hydroquinonebisphenol A mixtures, the yield of bisphenol A bischloroformate is improved if a stoichiometric excess of base (e.g., up to about 10% excess) is employed.

The amount of water is an essential feature of the method of this invention. It should be present in a molar ratio to alkaline earth metal ion of about 3-8:1, preferably about 5.0-5.5:1. If the molar ratio is less than 3:1, the various phases undergo inefficient mixing and yields are lower than desired. At values greater than 8:1, a substantial proportion of the hydroquinone dissolves in water and contact with phosgene, which remains in the organic phase, is minimized. Moreover, any hydroquinone chloroformates formed exist in the presence of relatively large amounts of hydroquinone, water and base, promoting formation of oligomeric hydroquinone carbonate bischloroformates as previously explained.

The proportion of organic liquid is not critical, provided a sufficiently fluid reaction mixture is formed. Most often, the amount of organic liquid is sufficient to yield a product concentration in the range of about 0.5–1.5 M, preferably about 0.8–1.2 M.

Various orders of addition of the reagents may be employed. For the most part, bisphenol and at least a portion of the organic liquid are initially present in the reaction vessel. Alkaline earth metal hydroxide may also be initially present; however, it is usually preferred to add it concurrently with the phosgene. It may be added in solid form, as an aqueous paste or as a slurry in the organic liquid, the latter mode generally being most convenient since slurries are easier to introduce by pumping than are solids or pastes. It is also within the scope of the invention, although usually not preferred, to add bisphenol and phosgene concurrently to the alkaline earth metal hydroxide.

As described in the aforementioned U.S. Pat. No. 4,638,077, the distributions of the monomeric mono- and bischloroformate species and higher oligomeric carbonate monoand bischloroformates in the reaction products produced by phosgenation of bisphenols have conventionally been determined by endcapping with phenol in the presence of triethylamine, followed by high pressure liquid chromatographic analysis. This method is successful for the determination of bisphenol A bischloroformate distributions according to the present invention. However, it cannot conveniently be employed with hydroquinone-derived products since the lower oligomeric hydroquinone carbonate diphenyl esters are almost totally insoluble in organic liquids such as methylene chloride, although the monomeric mono- and bis-phenyl esters are soluble.

It has been discovered that anthracene can be used as an internal standard in the capped bischloroformate product, and that the yield of monomeric hydroquinone bischloroformate can thus be determined. This is the method which was employed for the determination of hydroquinone product yields in the examples herein.

Following preparation of the bischloroformate composition by the method of this invention, solvent may be removed and individual components of the composition, such as monomeric bischloroformates, separated by conventional means such as distillation, chromatography, fractional crystallization or the like. Such operations are frequently unnecessary, however, since for many purposes the bischloroformate compositions may be used without solvent removal or purification.

The invention is illustrated by the following examples.

EXAMPLE 1

A 5-necked Morton flask fitted with a mechanical stirrer, solid carbon dioxide-acetone condenser, phosgene dip tube, thermometer and rubber septum was charged with 200 ml. of methylene chloride and 15 grams (200 mmol.) of calcium hydroxide. There were added, with vigorous stirring, 18 grams (1 mole) of water and 22 grams (200 mmol.) of hydroquinone, and phosgene was then passed into the mixture at 2–3 grams per minute, with vigorous stirring, until the stoichiometric amount (39.6 grams, or 400 mmol.) had been introduced. The mixture was then purged with nitrogen and an excess of water was added to remove residual phosgene, after which the organic layer was separated, washed with aqueous hydrochloric acid solution and dried. The yield of hydroquinone bischloroformate was found upon analysis to be 56% of theoretical.

EXAMPLE 2

A mixture of 27.5 grams (250 mmol.) of hydroquinone and 250 ml. of methylene chloride was vigorously stirred in the reaction vessel of Example 1 and phosgene was passed into the mixture at 2–3 grams per second, with vigorous stirring, until the stoichiometric amount had been introduced. There was simultaneously added a paste of 18.5 grams (250 mmol.) of calcium hydroxide in 23 grams (1.28 moles) of water. Following completion of phosgene addition, the reaction mixture was worked up as in Example 1. The yield of hydroquinone bischloroformate was 49% of theoretical.

EXAMPLE 3–5

Phosgene was passed at a rate of 2–3 grams per minute, with vigorous stirring, into mixtures of 11 grams (100 mmol.) of hydroquinone, 100 ml. of methylene chloride and various amounts of calcium hydroxide. When the stoichiometric amount of phosgene had been added, the reaction mixtures were worked up as described in Example 1. The proportions and product yields are listed in Table I.

TABLE I

| Example | $Ca(OH)_2$, mmol. | Bischloroformate, % yield |
|---|---|---|
| 3 | 100 | 55 |
| 4 | 150 | 62 |
| 5 | 200 | 41 |

EXAMPLES 6–9

Various mixtures of hydroquinone, methylene chloride, bisphenol A (in Examples 8 and 9) and calcium hydroxide in an equimolar amount with respect to bisphenol(s) were stirred vigorously and phosgene was introduced at a rate of 2–3 grams per minute, with simultaneous addition of water. When the stoichiometric amount of phosgene had been introduced, the mixtures were worked up as in Example 1. The relevant parameters are given in Table II.

TABLE II

| | Example | | | |
|---|---|---|---|---|
| | 6 | 7 | 8 | 9 |
| Hydroquinone, mmol. | 250 | 250 | 150 | 600 |
| Bisphenol A, mmol. | — | — | 100 | 400 |
| Water, moles | 1.28 | 1.28 | 1.28 | 5 |
| Percent yield: | | | | |
| Hydroquinone bischloroformate | 82 | 79 | 67 | 82 |
| Bisphenol A bischloroformate | — | — | 80 | 64 |

EXAMPLE 10

A 2-liter 5-necked Morton flask fitted similarly to that of Example 1 was charged with 55 grams (500 mmol.) of hydroquinone, 114 grams (500 mmol.) of bisphenol A and 680 ml. of methylene chloride. The mixture was allowed to equilibrate for about 10 minutes at 15°–20° C., after which phosgene was passed in at 3 grams per minute and there was simultaneously added a slurry of 77.8 grams (1.05 moles) of calcium hydroxide in 110 ml. of methylene chloride and 100 ml. of water. The addition rate of the calcium hydroxide mixture was 1.5 ml. per minute, and the temperature of the reaction mixture was maintained in the range of 15°–18° C. When the stoichiometric amount of phosgene had been introduced, stirring was continued for 30 minutes as the mixture was purged with nitrogen. There was then added 200 ml. of water, followed by a 50% aqueous sodium hydroxide solution to attain a pH of 8. During the purge and sodium hydroxide addition, the temperature was maintained below 20° C. The organic layer was separated and washed with aqueous hydrochloric acid solution. The yields of hydroquinone bischloroformate and bisphenol A bischloroformate were 75% and 85% of theoretical, respectively.

What is claimed is:

1. A method for preparing a bischloroformate composition which comprises passing phosgene into a vigorously agitated reaction mixture of water; a substantially inert, water-immiscible organic liquid; an alkaline earth metal hydroxide; and a dihydroxyaromatic composition selected from the group consisting of hydroquinone and mixtures of hydroquinone and bisphenol A containing at least 40 mole percent hydroquinone, said reaction mixture being maintained at a temperature in the range of about 10–40° C.; the molar ratio of water to alkaline earth metal ion in said reaction mixture being in the range of about 3–8:1.

2. A method according to claim 1 wherein the alkaline earth metal hydroxide is calcium hydroxide.

3. A method according to claim 2 wherein the organic liquid is methylene chloride 4. A method according to claim 3 wherein the molar ratio of calcium hydroxide to dihydroxyaromatic compounds in the dihydroxyaromatic composition is in the range of about 1–10:1.

5. A method according to claim 3 wherein the dihydroxyaromatic composition consists of hydroquinone.

6. A method according to claim 5 wherein the molar ratio of water to calcium hydroxide is in the range of about 5.0–5.5:1.

7. A method according to claim 6 wherein the hydroquinone and at least a portion of the methylene chloride are initially present in the reaction vessel.

8. A method according to claim 7 wherein the calcium hydroxide is added concurrently with the phosgene.

9. A method according to claim 8 wherein the calcium hydroxide is added as an aqueous paste.

10. A method according to claim 8 wherein the calcium hydroxide is added as a slurry in the methylene chloride.

11. A method according to claim 3 wherein the dihydroxyaromatic composition is a hydroquinone-bisphenol A mixture.

12. A method according to claim 11 wherein the molar ratio of water to calcium hydroxide is in the range of about 5.0–5.5:1.

13. A method according to claim 12 wherein the dihydroxyaromatic composition contains about 50–75 mole percent hydroquinone.

14. A method according to claim 12 wherein the dihydroxyaromatic composition and at least a portion of the methylene chloride are initially present in the reaction vessel.

15. A method according to claim 14 wherein the calcium hydroxide is added concurrently with the phosgene.

16. A method according to claim 15 wherein the calcium hydroxide is added as an aqueous paste.

17. A method according to claim 15 wherein the calcium hydroxide is added as a slurry in the methylene chloride.

* * * * *